(12) United States Patent
Reiffenrath et al.

(10) Patent No.: US 6,207,835 B1
(45) Date of Patent: Mar. 27, 2001

(54) PROCESS FOR THE PREPARATION OF ARYLMETAL COMPOUNDS AND THEIR REACTION WITH ELECTROPHILIC REAGENTS (75) Inventors: Volker Reiffenrath, Rossdorf; Hans Christian Stiasny, Griesheim, both of (DE)

(73) Assignee: Merck KGaA, Darmstadt (DE)

( * ) Notice: Subject to any disclaimer, the term of this patent is extended or adjusted under 35 U.S.C. 154(b) by 0 days.

(21) Appl. No.: 09/465,749

(22) Filed: Dec. 17, 1999

(30) Foreign Application Priority Data

Dec. 19, 1998 (DE) .............................................. 198 58 856

(51) Int. Cl.[7] ...................... C07D 211/06; C07D 319/06; C07F 7/26; C07C 41/01; C07C 43/02
(52) U.S. Cl. .......................... 546/226; 546/241; 549/374; 556/12; 568/640; 568/641; 568/643; 568/645; 568/660; 568/807
(58) Field of Search .............................. 549/374; 546/226, 546/241; 556/12; 568/640, 641, 643, 645, 660, 807

(56) References Cited

U.S. PATENT DOCUMENTS 5,210,304 * 5/1993 Balhouf et al. ...................... 564/440

FOREIGN PATENT DOCUMENTS

| 0238272 | 3/1987 | (EP) | ................................ | C07F/5/02 |
| 0440082 | 1/1991 | (EP) | ................................ | C07F/5/02 |
| WO89/02425 | 3/1989 | (WO) | ............................. | C07C/25/18 |

* cited by examiner

Primary Examiner—Mukund J. Shah
Assistant Examiner—Ben Schroeder
(74) Attorney, Agent, or Firm—Millen, White, Zelano & Branigan, P.C.

(57) ABSTRACT

Arylmetal compounds are prepared by deprotonation of aromatics which have a hydrogen atom in the ortho position relative to a halogen atom or a trifluoromethoxy group, using a suitable base or by halogen-metal exchange of haloaromatics using a suitable metalating reagent. The arylmetal compounds are prepared in a continuous-flow reactor. The arylmetal compound can be further reacted with an electrophilic reagent.

16 Claims, 2 Drawing Sheets

PROCESS FOR THE PREPARATION OF ARYLMETAL COMPOUNDS AND THEIR REACTION WITH ELECTROPHILIC REAGENTS

The invention relates to a process for the preparation of arylmetal compounds by deprotonation of aromatics which have a hydrogen atom in the ortho position relative to a halogen atom or a trifluoromethoxy group, using a suitable base or by halogen-metal exchange of haloaromatics using a suitable metalating reagent and their reaction with electrophilic reagents, characterized in that the arylmetal compounds are prepared in a continuous-flow reactor.

Substituted aromatics are useful intermediates for the synthesis of high-value-added end products or are themselves such end products for the electronics industry, such as, for example, liquid crystals, for crop protection, such as, for example, pesticides or for the preparation of pharmaceutically highly active substances, such as, for example, dopamine receptor blockers, antiemetics or antipsychotics.

This is true in particular of aromatics which are substituted in the ortho position relative to a halogen atom or a trifluoromethoxy group.

A variety of methods for the preparation of such compounds are described in the literature.

Thus, for example, the metalation, described by D. L. Ladd in J. Org. Chem. 46, 203 (1981), of 1,4-difluorobenzene with butyllithium at <−65° C. gives 1-lithium-2,5-difluorobenzene, which is reacted at the same (low) temperature with trimnethyl borate to give dimethyl 2,5-difluorobenzeneboronate (Scheme 1).

The boronate is oxidized with hydrogen peroxide to give the corresponding phenol.
This reaction sequence is also described in WO 89/2425 for the preparation of 2,3-difluorophenol, the reaction temperatures being unchanged and the reaction conditions being changed only slightly (Scheme 2).

WO 89/2425 further describes the preparation of liquid-crystalline 2,3- or 2',3'-difluoro-p-terphenylene starting from 1,2-difluorobenzene. WO 89/8629 describes the synthesis of other liquid-crystalline compounds which have a 2,3-difluoro-1,4-phenylene group. In the processes described therein, the 1,2-difluorobenzene or 1-substituted 2,3-difluorobenzene is deprotonated using a strong base, normally using n-butyllithium, and the resulting 2,3-difluorophenyllithium compound is reacted with an electrophilic reagent.

Furthermore, the o-fluorophenyl derivatives can be prepared from the corresponding o-fluorobromobenzenes by reaction with magnesium to give o-fluorophenylmagnesium bromide and subsequent derivatization (e.g. EP 02 38 272). Here too, it is absolutely necessary to operate at low temperatures.

Analogously to the ortho-fluoroarylmetal compounds, other ortho-haloarylmetal compounds are also obtainable using ortho-position hydrogen with the help of a base at very low temperatures (e.g. Houben-Weyl, Methoden der organischen Chemie [Methods of Organic Chemistry], Vol. 13/1, 122–123, Stuttgart 1970).

According to DE 42 19 281, it is also possible to replace those hydrogen atoms which are in the ortho position relative to a trifluoromethoxy group. A pre-requisite for this process is likewise the maintenance of very low temperatures.

As well as the possibility of obtaining the arylmetal compounds by deprotonation, it is also possible to utilize halogen-metal exchange using a suitable metalating reagent to prepare the desired compounds (e.g. Houben-Weyl, Methoden der organischen Chemie [Methods of Organic Chemistry], Vol. 13/1, 152–156, Stuttgart 1970 and Vol. 13/2a, 172–173, Stuttgart 1973). Particularly when the arylmetal compounds are halogenated in the ortho position or are substituted in this position by the trimethoxy group, it is also necessary during halogen-metal exchange and during further reaction with electrophilic reagents to maintain very low temperatures.

The reason for the low reaction temperatures is the poor stability of the ortho-haloarylmetal compounds.

For example, 2,3-difluorophenyllithium derivatives eliminate lithium fluoride above −50° C., forming 1-fluoro-2,3-benzyne derivatives, which further react in an uncontrolled manner to give unknown secondary products.

At −50° C. the rate of the decomposition reaction of the 2,3-difluorophenyllithium derivatives is still slow, but proceeds in an explosive manner at −25° C. (critical temperature −22.5° C.), the 2,3-difluorophenyllithium derivatives decomposing suddenly.

However, other ortho-haloarylmetal compounds usually have an even lower stability than the ortho-fluoroarylmetal compounds, meaning that the decomposition reactions occur at considerably lower temperatures.

For example, from Bull. Soc. Chim. France 1986 No. 6, 925–929, it is known that chloroaryl compounds metalated in the ortho position readily eliminate chloride in an exothermic reaction, as a result of which arynes are formed, which give rise to the formation of undesired by-products.

For relatively large batches on a production scale, these processes for the preparation of ortho-halo- and ortho-trifluoromethoxyarylmetal compounds are not suitable since failure of the coolant would result in an increased risk of explosion.

Remedies are provided in this connection by processes described in EP 440 082 B1 and DE 42 01 308 C1, in which the electrophilic reagent and the aromatic are initially introduced and the base can be added at room temperature. In the process, the intermediate ortho-haloaryllithium compounds are immediately scavenged in situ by the respective electrophilic reagent, thus avoiding an accumulation of the unstable component and thus haza rdous secondary reactions.

However, these processes give unsatisfactory yields when a haloaromatic is reacted with an electrophilic reagent which reacts with the lithium base used at a similarly rapid rate to that of the haloaromatic to be metalated or even more rapidly than the latter. For example, drops in yield occur when, according to the processes described in EP 440 082 B1, a haloaromatic is to be reacted with a ketone in the presence of butyllithium or lithium diisopropylamide to give the corresponding lithium alkoxide. In this case, the addition of the base or the enolization of the ketone is at the fore, and the desired reaction does not take place (Scheme 3).

Scheme 3

X': F, Cl

Particularly for such reactions, the traditional processes are hitherto still unavoidable.

The very low temperatures which usually have to be maintained particularly in the case of the sensitive ortho-halometal compounds have proven to be a disadvantage if the intention is to deprotonate aromatics having only a very weakly acidic hydrogen atom. Higher rates of reaction and thus often also better yields, which can be achieved at relatively high temperatures, are excluded for the prior art processes with the exception of the processes described in EP 440 082 B1 and DE 42 01 308 C1.

Finally, the prior art processes, being typical batch processes, are time-consuming and costly to carry out, since cleaning, changeover and no-load times limit the optimum capacity of the plants used.

More recent developments in the electronics industry have resulted in a considerable demand for liquid crystals which have a mono- or polyfluorinated 1,4-phenylene radical, in particular a 2,3-difluoro- or 2,6-difluoro-1,4-phenylene radical. The object of the present invention was to find a preparation process for arylmetal compounds and in particular for ortho-haloarylmetal compounds which does not have the described disadvantages of the processes hitherto and it can be carried out safely on an industrial scale.

It has now been found that the preparation of arylmetal compounds by deprotonation of aromatics which have a hydrogen atom in the ortho position relative to a halogen atom or a trifluoromethoxy group, using a suitable base or by halogen-metal exchange of haloaromatics using a suitable metalating reagent can be carried out safely even at relatively high temperatures and with a high yield if the arylmetal compounds are prepared in a continuous-flow reactor and are reacted immediately after their formation with a suitable electrophilic reagent.

Here, the reaction of the arylmetal compounds formed can be carried out by allowing the arylmetal compounds to pass into a solution or a melt of an electrophilic reagent outside of the continuous-flow reactor or by introducing the electrophilic reagent into the continuous-flow reactor directly after formation of the arylmetal compounds and allowing it to react therein.

Preference is given to introducing the electrophilic reagent into the continuous-flow reactor directly after formation of the arylmetal compounds.

The process according to the invention enables high yields to be achieved using those electrophilic reagents which could not be used or could be used only with yield limitations in the process according to EP 440 082 B1 and DE 42 01 308 C1 because of their preferred reaction with the base.

Because of the relatively small reaction volume of the continuous-flow reactor, only small amounts of the temperature-sensitive intermediate are ever present in the system. Decomposition of this amount does not generally represent any danger. As a result, it is possible to carry out the process safely even at temperatures close to or even above the decomposition point of the unstable organometallic compound, at a high throughput rate.

High temperatures can lead to an increase in yield during the reaction of less acidic haloaromatics with bases, since the rate of deprotonation is increased as a result.

In addition, when carrying out the process according to the invention at relatively high temperatures, a saving in energy is achieved using lower cooling output. As a result of the fact that the continuous-flow reactor generally has a ratio of cooling area to volume of medium to be cooled which is considerably better than the normal stirred apparatus, high throughputs can be achieved even in relatively small plants. In view of its simple construction, the continuous-flow reactor is also the significantly more cost-effective alternative to the stirred apparatus with low-temperature unit.

The invention thus provides a process for the preparation of arylmetal compounds by deprotonation of aromatics which have a hydrogen atom in the ortho position relative to a halogen atom or a trifluoromethoxy group, using a suitable base or by halogen-metal exchange of haloaromatics using a suitable metalating reagent and their reaction with electrophilic reagents, characterized in that the arylmetal compounds are prepared using a continuous-flow reactor.

In particular, the invention relates to a process for the preparation of ortho-haloarylmetal compounds by deprotonation of aromatics which have a hydrogen atom in the ortho position relative to a halogen atom, using a suitable base or their halogen-metal exchange of haloaromatics using a metalating reagent and their reaction with electrophilic reagents, characterized in that the ortho-haloarylmetal compounds are prepared in a continuous-flow reactor.

A preferred subject-matter of the invention is a process for the preparation of ortho-haloarylmetal compounds and their reaction with corresponding electrophilic reagents to give the compounds of the formula I, where

Q is F, Cl or Br,

R¹ is H, F, Cl, Br, CN, alkyl, alkenyl, alkoxy, alkenyloxy having in each case up to 18 carbon atoms or a mesogenic group, W, X and Y in each case independently of one another are N, CH, CCN or CF, and E is in which

R² is alkyl, alkoxy, alkenyl, alkenyloxy having up to 15 carbon atoms or a mesogenic radical,

M is Li, K, MgBr, MgCl or MgI, s is 0 or 1, $BX_2^2$ is a group of the formula —B(OR³)(OR⁴), or a trioxatriborinone radical of the formula in which Z is R³ and R⁴ are H, alkyl, alkenyl or cycloalkyl having in each case up to 10 carbon atoms or, taken together, are an alkylenediyl group of the formula —(CH₂)ₙ— or —CH₂CHR⁵—CH₂—, in which n is 2, 3 or 4 and R⁵ is alkyl, alkoxy or alkenyl having up to 18 carbon atoms or a mesogenic radical, and S¹ is a trihydrocarbylsilyl group of the formula —Si(R⁶)₃ in which R⁶ in each case independently of one another is an aliphatic, cycloaliphatic, araliphatic or aromatic radical having up to 12 C atoms, preferably up to 7 C atoms,

TiX₃ is a radical of the formula TiBr₃, TiCl₃ or Ti(OR₃)₃

ZnX⁴ is a radical of the formula ZnBr, ZnCl, ZnR³ or ZnOR³ characterized in that the ortho-haloarylmetal compounds are prepared in a continuous-flow reactor.

A particularly preferred subject-matter of the invention is a process for the preparation of ortho-haloarylmetal compounds and their reaction with corresponding cyclohexanones to give the compounds of the formula IA

IA where

Q, R¹, R², M,

W, X and Y have the meanings given above, characterized in that the ortho-haloarylmetal compounds are prepared in a continuous-flow reactor.

In particular, the invention relates to those processes in which R¹, R², and/or R⁵ is a mesogenic group of the formula II, where R⁰ is F, CN, an alkyl or alkenyl radical having up to 15 carbon atoms which is unsubstituted or monosubstituted by CN, halogen or CF₃, where in these radicals, in addition, one or more CH₂ groups in each case independently of one another can be replaced by —S—, —O—, —CO—, —CO—O—, —O—CO— or —O—CO—O—such that S and/or O atoms are not linked directly to one another, Z¹ and Z² in each case independently of one another are —CH₂CH₂—, —C≡C—, —CH₂O—, —OCH₂—, —CO—O—, —O—CO—, —CH=N—, —N=CH—, —CH₂S—, —SCH₂—, a single bond or an alkylene group having from 3 to 6 carbon atoms, in which, in addition, a CH₂ group can be replaced by —O—, —CO—O—, —O—CO—, —CHhalogen— or —CHCN—, and $A^1$ and $A^2$ in each case independently of one another are
a) a trans-1,4-cyclohexylene radical, in which, in addition, one or more non-adjacent $CH_2$ groups can be replaced by —O— and/or —S—,
b) a 1,4-phenylene radical, in which, in addition, one or two CH groups can be replaced by N,
c) a radical from the group consisting of 1,3-cyclobutylene, 1,3-bicyclo(1,1,1)-pentylene, 1,4-cyclohexenylene, 1,4-bicyclo(2,2,2)octylene, piperidine-1,4-diyl, naphthalene-2,6-diyl, decahydronaphthalene-2,6-diyl and 1,2,3,4-tetrahydronaphthalene-2,6-diyl
where the radicals (a) and (b) can be substituted by CN or halogen such as F, and
m is 0, 1 or 2.

The ortho-haloaryl derivatives prepared by the process according to the invention include mono-, di-, tri- and tetrahalophenyl derivatives and pentahalophenyl derivatives. Halo refers to fluoro, chloro, bromo, and iodo, preferably fluoro.

Particular preference is given to an embodiment of the invention where the arylmetal compounds obtained by metalation are reacted with a metal halide such as, for example, $ZnCl_2$ or $ZnBr_2$, or other metal compounds, such as, for example, $Ti(OR^3)_4$, preferably titanium tetraisopropoxide, titanium tetramethoxide, titanium tetraethoxide or titanium tetra-n-propoxide. The compounds obtained as a result of this transmetalation are generally more thermally stable than the starting materials and can likewise be reacted with electrophilic reagents.

2-Halopyridin-3-yl derivatives can also be prepared by the process according to the invention. Whether other substituents are present in the aromatic ring in addition to the halo substituents is unimportant when carrying out the process according to the invention. Other substituents which may be mentioned are, for example, alkyl, alkenyl or alkoxy groups, chlorine and bromine or mesogenic groups. In addition, the halogenated aromatic rings can also be constituents of condensed ring systems, such as, for example, of naphthalenes, di- and tetrahydronaphthalenes or of 2,3,4,5-tetrahydro-1H-3-benzazepine derivatives.

For the sake of simplicity, in the text below Phe is a 1,4-phenylene group, in which one or two CH groups can also be replaced by N, and the 1,4-phenylene group can also be substituted by one or two halogen atoms.

ArF is a fluorinated 1,4-phenylene group of the formula where $L^1$, $L^2$ and $L^3$ in each case independently of one another are H or F.

Cyc is a trans-1,4-cyclohexylene radical, in which one or more non-adjacent $CH_2$ groups can also be replaced by —O—, and which can also be substituted by halo, preferably F, or CN.

E is a group which has been introduced by the reaction according to the invention.

Preference is given to using ketones, carboxamides or aldehydes as electrophilic reagent.

Preferred electrophilic reagents are the following compounds of the formulae IIIa to IIIq:

in which $R^2$ is alkyl, alkoxy, alkenyl, alkenyloxy having from 1 to 15 carbon atoms or a mesogenic group corresponding to the formula II, m is 1 or 2, and $X^1$ is Cl, Br, iodine, a toluene- or benzenesulfonic acid group or a perfluoroalkylsulfonic acid group. Halogens preferably mean F, Cl, Br, I, in particular Br or I. $R^3$ and s have the meaning given above.

Silylation reagents are the compounds of the formula IIIm S'—L, in which SI has the given meaning and L is a leaving group, in particular compounds of the formulae IIIm1 to IIIm8:

IIIm1

IIIm2

IIIm3

IIIm4

IIIm5

IIIm6

IIIm7

IIIm8

To prepare the compounds of the formula I in which E is $B(OR^3)(OR^4)$, trialkyl borates of the formula IIIn1 $B(OR^3)_2(OR^4)$ are preferably suitable.

Particular preference is given to using the electrophilic reagents of the formulae IIIa1 to IIIn1 for the process according to the invention:

IIIa1

IIIa2

IIIa3

IIIa4

IIIa5

IIIa6

IIIa7

-continued

IIIq1

(H₃C)₃SiCl
IIIm1

(H₃C)₂(tert-C₄H₉)SiCl
IIIm5

B(OR³)₂(OR⁴)
IIIn1 in which $R^7$ is preferably an alkyl, alkoxy, alkenyl or alkenyloxy radical having up to 12 carbon atoms, $L^1$, $L^2$, $L^3$ and $L^4$ are H or F, and $X^1$ has the meaning given above.

Further preferred electrophilic reagents for the process according to the invention are the ketones of the formula IIIo IIIo in which

R⁸ and R⁹ are independently of one another an alkyl or alkenyl radical having up to 15 carbon atoms and which is unsubstituted or monosubstituted by CN, halogen or CF₃, where in these radicals one or more CH₂ groups in each case independently of one another can be replaced by —S—, —O—, A, —CO—, —CO—O—, O—CO— or —O—CO—O such that —S— and/or —O— atoms are not linked directly to one another.

A is in each case independently of one another
  (a) a trans-1,4-cyclohexylene radical in which one or more non-adjacent CH₂ groups can also be replaced by —O— and/or —S—.
  (b) A 1,4-phenylene radical in which one or two CH groups can also be replaced by N.
  (c) A radical from the group consisting of 1,3-cyclobutylene, 1,3-bicyclo(1,1,1)pentylene, 1,4-cyclohexenylene, 1,4-bicyclo(2,2,2)octylene and piperidine-1,4-diyl, where the radicals (a) (b) and (c) can be mono- or polysubstituted by R⁸, R⁹, CN or halogen.

Particularly preferably, the compounds of the formulae IV1 to IV10 are metalated by the process according to the invention.

IV1

IV2

IV3

IV4

IV5

IV6

IV7

IV8

IV9

IV10 in which B is H, Br or I, Q and $R^1$ have the meanings given, and $L^1$, $L^2$, $L^3$ and $L^4$ independently of one another are H or F. $Q^1$ is F or Cl, in particular F.

In the preferred starting compounds of the formulae IV1 to IV10, from which the arylmetal compounds are produced by deprotonation using a suitable base, the radical B assumes the meaning H.

In the preferred starting compounds of the formulae IV1 to IV10, from which the arylmetal compounds are produced by halogen-metal exchange using a suitable metalating reagent, the radical B assumes the meaning Br or I, particularly preferably the meaning Br.

Preferably, only one of the radicals $L^1$ and $L^2$ is H, and the other is F.

The compounds of the formula I prepared by the process of the invention include those of the formulae Ia to Ii:

Ia

Ib

Ic

Id

Ie

If

Ig

Ih

Ii

Of these, the compounds of the formulae Ia, Ib, Id and Ig are particularly preferred. In said compounds of the formulae Ia to Ii, $R^1$ is preferably H. alkyl or alkoxy having in each case from 1 to 12 carbon atoms, or a mesogenic radical, particular preference being given according to the process of the invention to the compounds of the formula Ib in which $R^1$ is H or alkoxy having from 1 to 12, in particular from 2 to 4, carbon atoms.

The compounds of the formulae Ib, Ie, If and Ig are particularly suitable as intermediates for the preparation of liquid crystals having a 2,3-difluoro-1,4-phenylene or 2,3-difluoro-1,4-phenylenoxy structural unit. The compounds of the formula I which have a mesogenic radical of the formula II include the preferred compounds of the formulae I1 to I13:

$$R^0—A^1—ArF—E \qquad \text{I1}$$

$$R^0—A^1—Z^1—ArF—E \qquad \text{I2}$$

$$R^0—A^1—A^2—ArF—E \qquad \text{I3}$$

$$R^0—A^1—A^2—Z^2—ArF—E \qquad \text{I4}$$

$$R^0—A^1—Z^1—A^2—ArF—E \qquad \text{I5}$$

$$R^0—A^1—Z^1—A^2—Z^2—ArF—E \qquad \text{I6}$$

$$R^0—A^1—A^2—A^2—ArF—E \qquad \text{I7}$$

$$R^0—A^1—Z^1—A^2—A^2—ArF—E \qquad \text{I8}$$

$$R^0—A^1—A^2—Z^2—A^2—ArF—E \qquad \text{I9}$$

$$R^0—A^1—A^2—A^2—Z^2—ArF—E \qquad \text{I10}$$

$$R^0—A^1—Z^1—A^2—Z^2—A^2—ArF—E \qquad \text{I11}$$

$$R^0—A^1—Z^1—A^2—A^2—Z^2—ArF—E \qquad \text{I12}$$

$$R^0—A^1—A^2—Z^2—A^2—Z^2—ArF—E \qquad \text{I13}$$

Of these, the compounds of the formulae I1, I2, I3, I4 and I7 are particularly preferred.

Of the compounds of the formulae I1, those of the formulae I1a to I1c are particularly preferred.

Alkyl-Phe-ArF—E  I1a

Alkyl-Cyc-ArF—E  I1b

Alkoxy-Phe-ArF—E  I1c

Of the compounds of the formula I2, those of the formulae I2a to I2i are particularly preferred.

Alkyl-Phe-CH₂CH₂—ArF—E  12a

Alkyl-Phe-CH₂O—ArF—E  12b

Alkyl-Phe-C≡C—ArF—E  12c

Alkoxy-Phe-C≡C—ArF—E  12d

Alkoxy-Phe-CH₂O—ArF—E  12e

Alkoxy-Phe-CH₂CH₂—ArF—E  12f

Alkyl-Cyc-CH₂CH₂—ArF—E  12g

Alkyl-Cyc-CH₂O—ArF—E  12h

Alkyl-Cyc-C≡C—ArF—E  12i

The following group of compounds includes the particularly preferred compounds I14 to I28, which can be prepared by the process according to the invention.

I14

I15

I16

I17

I18

I19

I20

I21

I22

I23

I24

I25

I26

I27

[Structure: benzene ring with F (top), F (bottom), X₂²B— on left, —R¹ on right]

I28

[Structure: benzene ring with F, L¹, L², L³ substituents, S'— on left, —R¹ on right]

in which R¹, R⁷, BX₂², M and SI assume the meanings given above. L¹, L² and L³ independently of one another are H or F.

In the preferred compounds of the formulae above and below, R¹ and R² independently of one another are alkyl groups having preferably from 1 to 10 carbon atoms, alkoxy groups, alkenyl groups or alkenyloxy groups having, preferably, in each case from 1 to 10 carbon atoms.

Particularly preferred alkyl groups are n-hexyl, n-pentyl, n-butyl, i-butyl, propyl, i-propyl, methyl and ethyl, in particular methyl; particularly preferred alkoxy groups are n-hexoxy, n-pentoxy, n-butoxy, i-butoxy, n-propoxy, i-propoxy, methoxy and ethoxy, in particular methoxy; particularly preferred alkenyl groups are hexenyl, pentenyl, butenyl and allyl.

In the preferred compounds of the formulae above and below, the alkyl radicals in which, in addition, a CH₂ group (alkoxy or oxaalkyl) can be replaced by an O atom, can be straight-chain or branched. They preferably have 2, 3, 4, 5, 6, 7, 8, 9 or 10 carbon atoms and are accordingly preferably ethyl, propyl, butyl, pentyl, hexyl, heptyl, octyl, nonyl, decyl, propoxy, ethoxy, butoxy, pentoxy, hexoxy, heptoxy, octoxy, nonoxy or decoxy, and also undecyl, dodecyl, undecoxy, dodecoxy, 2-oxapropyl (=2-methoxypentyl), 2-, 3- or 4-oxapentyl, 2-, 3-, 4- or 5-oxahexyl, 2-, 3-, 4-, 5- or 6-oxaheptyl.

A¹ and A² are preferably Cyc or Phe. In the compounds of the formulae above and below, Phe is preferably a 1,4-phenylene group (Ph), a 1,4-phenylene group (PheX) mono- or disubstituted by F or CN, a pyrimidine-2,5-diyl group (Pyr), a pyridine-2,5-diyl group (Pyn), a pyrazine-3,6-diyl group or a pyridazine-2,5-diyl group, particularly preferably Ph, PheX, Pyr or Pyn. The compounds prepared by the process according to the invention preferably contain no more than one 1,4-phenylene group in which one or two CH groups have been replaced by N. Cyc is preferably a 1,4-cyclohexylene group. However, particular preference is given to compounds of the formula I in which one of the groups A¹ and A² is a 1,4-cyclohexylene group substituted by CN or F in the 1- or 4-position, and the nitrile group or the fluorine atom is in an axial position, i.e. the group A¹ or A² has the following structure:

[Structure: cyclohexyl with CN substituent; cyclohexyl with F substituent]

Particular preference is given to compounds of the formula I and of the above subformulae which contain a-Phe- Phe- grouping. -Phe-Phe- is preferably -Ph-Ph-, Pyr-Phe or Ph-Pyn. Particular preference is given to the groups

[Structure: pyrimidine-phenyl] and

[Structure: phenyl-pyridine]

also 4,4'-biphenylyl which is unsubstituted or mono- or polysubstituted by fluorine.

Particular preference is given to compounds of the formula I and of the subformulae below which contain a 2,3-difluoro-1,4-phenylene group.

The groups Z¹ and Z² are in each case independently of one another preferably a single bond, secondarily preferably —C≡C— or —CH₂CH₂— groups. Particularly preferred are compounds of the formulae I in which a group Z¹ is —CH₂CH₂—. Compounds of the formulae above and below having branched wing groups R¹ can be of importance.

Branched groups of this type generally contain not more than two chain branches. R¹ is preferably a straight-chain group or a branched group with not more than one chain branch.

Preferred branched radicals are isopropyl, 2-butyl(=1-methylpropyl), isobutyl(=2-methylpropyl), tert-butyl, 2-methylbutyl, isopentyl(=3-methylbutyl), 2-methylpentyl, 3-methylpentyl, 4-methylpentyl, 2-ethylhexyl, 5-methylhexyl, 2-propylpentyl, 6-methyl-heptyl, 7-methyloctyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy, 2-oxa-3-methylbutyl, 3-oxa-4-methylpentyl.

The radical R¹ can also be an optically active organic radical containing an asymmetric carbon atom. The asymmetric carbon atom is then preferably linked to two differently substituted carbon atoms, an H atom and a substituent chosen from the group consisting of fluorine, alkyl or alkoxy having in each case from 1 to 5 carbon atoms, and CN. The optically active organic radical R preferably has the formula, $$—X'—Q'—\underset{Y'}{C^*H}—R'$$

in which
X' is —O—, —S— or a single bond,
Q' is alkylene having from 1 to 5 carbon atoms, in which, in addition, a CH₂ group not linked to X' can be replaced by —O—, or a single bond,
Y' is CN, F, CF₃, methyl or methoxy, and
R' is an alkyl group having from 1 to 15 carbon atoms different from Y', in which, in addition, one or two non-adjacent CH₂ groups can be replaced by —S—, —O—.
X' is preferably a single bond.
Q' is preferably —CH₂—, —CH₂CH₂—, —CH₂CH₂CH₂— or a single bond, particularly preferably a single bond.
Y' is preferably CH₃, —CN or F, particularly preferably CN or F.
R' is preferably straight-chain or branched alkyl or alkoxy having from 1 to 10, in particular having from 1 to 7, carbon atoms.

Of the compounds of the formulae I, IA, and Ia to Ii, preference is given to those in which at least one of the radicals present therein has one of the preferred meanings given.

The compounds of the formula IV required as starting materials,

IV in which Q, $R^1$, W, X and Y have the meanings given, and B is H or halogen, preferably H, Br or I, are known or are prepared by methods known per se, as described in the literature (e.g. in standard works such as Houben-Weyl, Methoden der organischen Chemie [Methods of Organic Chemistry], Georg-Thieme-Verlag, Stuttgart), under reaction conditions which are known and suitable for said reactions. Use can also be made here of variants which are known per se but which are not mentioned here in greater detail.

The metal alkoxides produced during the reaction of arylmetal compounds with electrophilic reagents such as ketones, aldehydes or oxiranes are worked up under aqueous conditions to give the corresponding alcohols, which can be further processed by known methods. It is likewise possible to further process the metal alkoxides directly by known methods.

Other possible uses for the compounds prepared by the process according to the invention are described, for example, in EP 440082, incorporated herein by reference.

The following schemes give preferred further processing possibilities:

-continued

DAST: Diethylaminosulfur trifluoride

The reaction procedure of the process according to the invention is simple, where firstly the arylmetal compounds are prepared by reacting the starting materials at temperatures of from −100° C. to +100° C., preferably from −40° C. to +40° C., in particular at −35° C. to 0° C. in a continuous-flow reactor. The arylmetal compounds formed are then preferably reacted with an electrophilic reagent at the same temperature or at a higher temperature. The arylmetal compound can in this case be introduced into a melt or a solution of the electrophilic reagent, or the electrophilic reagent can be reacted with the arylmetal compound in a continuous-flow reactor.

Figure 1:
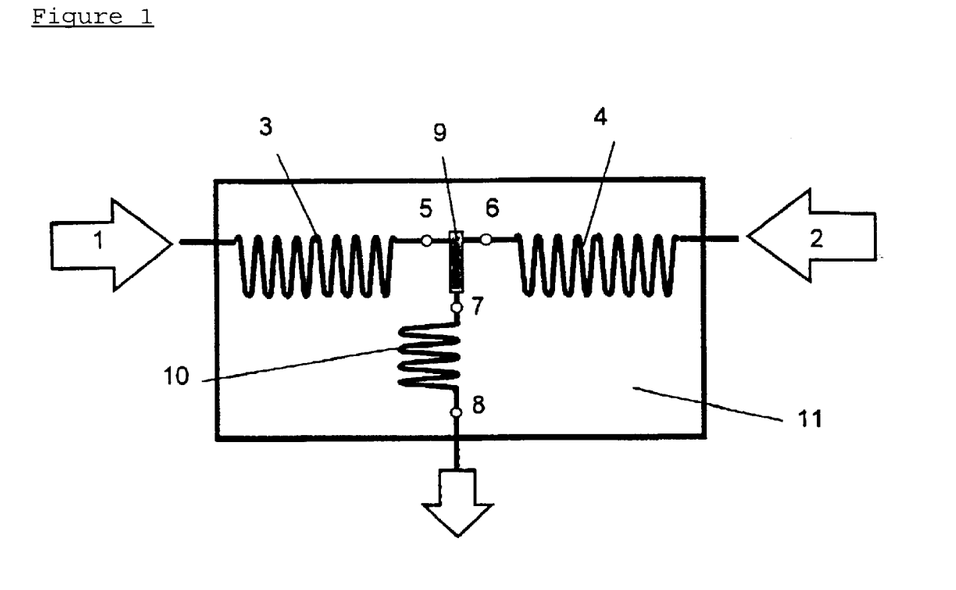
FIG. 1 illustrates an embodiment of a continuous-flow reactor for use in accordance with the process of the invention having pumps for the introduction of stalling materials.

The continuous-flow reactor preferably has the structure given diagrammatically in FIG. 1. In the figure, 1 and 2 are pumps for the starting materials, 3 and 4 are condensers for the starting materials, 5, 6, 7 and 8 are temperature measurement points, 9 is a mixer for the reactants, preferably a static mixer, 10 is the product condenser and 11 is the cooling medium temperature-regulated by a thermostat.

The starting materials are accordingly brought to react in a defined mass or volume stream in the mixer 9 via the condensers 3 and 4, and the product, after passing through the product condenser 10, is introduced into a solution or a melt of the electrophilic reagent.

Figure 2:
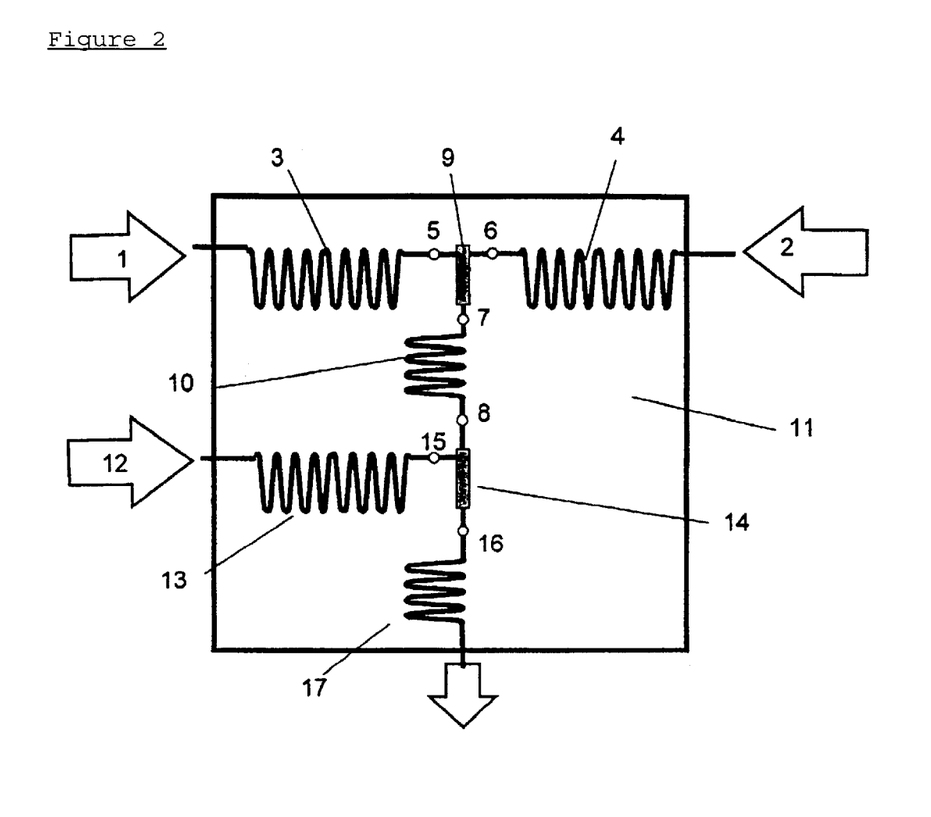
FIG. 2 illustrates a further embodiment of a continuous-flow reactor for use in accordance with the process of the invention which has an additional pump for the introduction of electrophilic reagent.

In a further preferred embodiment of the invention, the continuous-flow reactor has the structure given diagrammatically in FIG. 2. Here, the numbers 1 to 11 have the meanings given for FIG. 1, while 12 is a pump for the electrophilic reagent to be reacted, 13 is the condenser for the electrophilic reagent, 14 is a further mixer, preferably a static mixer, 15 and 16 are temperature measurement points and 17 is a condenser for the compounds of the formula I formed.

In such an apparatus it is, accordingly, possible to react the arylmetal compound formed in the mixer 9 continuously with a suitable electrophilic reagent.

Suitable static mixers are preferably also micromixers, which are sold, for example, by Sulzer, Germany or by Kenics.

The starting materials are usually introduced into the continuous-flow reactor in identical molar amounts, although it can also be advantageous to use one or two components in excess.

The starting materials, i.e., the aromatic to be metalated, base or metalating reagent and electrophilic reagent can be introduced into the continuous-flow reactor either in the melt or in a suitable solvent. Here, the starting materials can be dissolved in the same solvents or in different solvents. However, a prerequisite is the miscibility of the solvents used. Preference is given to using inert solvents which are conventionally suitable for reactions with strong bases or metalating reagents, e.g. ethers such as diethyl ether, tetrahydrofuran or methyl tert-butyl ether, hydrocarbons such as pentane, hexane, heptane, benzene, toluene, xylene or cyclohexane or mixtures of said solvents. To these solvents it is also possible to add cosolvents, such as, for example, hexamethylphosphoric triamide (HMPt), tetramethylethylenediamine (TMEDA), dimethylpropyleneurea (DMPU) or crown ethers, such as 18-crown-6. The amount of solvent is unimportant, it being possible in general to use from 100 to 1000 g of solvent per mole of the aromatic compounds to be metalated.

Bases used for the deprotonation of the haloaromatics and trifluoromethoxyaromatics are the bases used in the prior art processes.

These are preferably metal amides, in particular lithium amide, lithium, sodium or potassium dialkylamide, such as, for example, lithium dimethylamide, lithium diethylamide or lithium, sodium or potassium diisopropylamide, lithium piperidide, lithium, sodium or potassium bis(trimethylsilyl) amide or lithium, sodium or potassium 2,2,6,6-tetramethylpiperidide. In general, the lithium amides are particularly preferred.

The metal amides can be used directly or prepared in situ by reaction of the corresponding amines with an alkylmetal or arylmetal compound.

Preference is given to an embodiment of the process according to the invention in which catalytic amounts of an amine, preferably of a secondary amine such as diisopropylamine or 2,2,6,6-tetramethylpiperidine or bis (trimethylsilyl)amine, are used, which is converted into the corresponding metal amide by addition of an alkylmetal or arylmetal compound. After deprotonation of an ortho-halo- or trifluoromethoxyaromatic by this metal amide, the amine formed in the reaction is converted into the metal amide again by alkylmetal or arylmetal compound present. The use of catalytic amounts of the amine increases the yield of arylmetal compound and the rate of deprotonation.

A catalytic amount of the amine preferably means from 0.1 to 90 mol %, in particular from 0.2 to 30 mol % and very particularly preferably from 1 to 15 mol %, based on the compound to be deprotonated.

Also preferred for the deprotonation of the halo- or trifluoromethoxyaromatics are alkyl- or arylmetal compounds which are in customary use in organic chemistry (e.g. House: Modern Synthetic Reactions, $2^{nd}$ ed., Benjamin 1972, 547). Particularly suitable alkyl- and arylmetal compounds are n-butyllithium, sec-butyllithium, tert-butyllithium, methyllithium, ethyl-lithium, n-propyllithium, i-propyllithium, hexyllithium or phenyllithium. It is, however, also possible to use all other alkylmetal compounds which are known but not mentioned here specifically. Although the alkyl- and aryllithium compounds are preferred, it is also possible to use, for example, alkylpotassium compounds, which are preferably prepared in situ from potassium tert-butoxide and alkyllithium (e.g. Angew. Chem. Int. Ed. Engl. 12, 508 1973).

The metalating reagents used for the halogen-metal exchange on haloaromatics are the reagents used in the known processes. These are preferably alkylmetal compounds such as, for example, n-butyllithium, sec-butyllithium, tert-butyllithium, methyllithium, ethyllithium, n-propyllithium, i-propyllithium, hexyllithium or phenyllithium, in particular n-butyllithium, tert-butyllithium and methyllithium. It is, however, also possible to use all other alkylmetal compounds which are known but which are not mentioned here specifically, such as, for example, alkyl Grignard compounds.

Alkyllithium compounds are particularly preferred.

Preference is given to the process according to the invention for the preparation of aryllithium compounds and their reaction with electrophilic reagents.

For the process according to the invention for the preparation of arylmetal compounds by deprotonation, preference is given to using those aromatics which have a hydrogen atom in the ortho position relative to a fluorine or a chlorine atom or a trifluoromethoxy group.

For the process according to the invention for the preparation of arylmetal compounds by halogen-metal exchange, preference is given to using those aromatics which have a bromine or iodine atom which is replaced during metalation.

Suitable electrophilic reagents are preferably said compounds of the formulae IIIa to IIIn1, preferably cyclohexanones such as 4-alkyl-, alkoxy-, alkenyl-, alkenyloxy- or cycloalkylcyclohexanones or 4-arylcyclo-hexanones, or else simple aliphatic or unsaturated ketones such as acetone, butanone, 2-pentanone, methyl vinyl ketone, diethyl ketone, 2-hexanone, 3-hexanone, methyl isobutyl ketone, ethyl isopropyl ketone, diisopropyl ketone, ethyl isobutyl ketone, isobutyl isopropyl ketone, 2-heptanone, 3-heptanone, 4-heptanone, diisobutyl ketone, methyl vinyl ketone, mesityl oxide, acetonylacetone, benzylideneacetone, dibenzalacetone, pinacolone, ethyl tert-butyl ketone, phenylacetone, acetophenone, benzophenone, menthone, phorone, ketoglutaric ester, levulinic ester, diacetone acrylamide, isomethadone, normethadone, pseudoionone, ionone, dipipanone, norpipanone, teprenone, hygrine, cuscohygrine, 3-indolylacetone, phenadoxone, nabumetone or solanone, n-alkyl halides having from 1 to 16 carbon atoms, in particular n-alkyl bromides and iodides, such as, for example, methyl, ethyl, propyl, butyl, pentyl, hexyl, heptyl, octyl or nonyl bromide or methyl, ethyl, propyl, butyl, pentyl, hexyl, heptyl, octyl or nonyl iodide, n-alkanals having from 2 to 16 carbon atoms, in particular acetaldehyde, propionaldehyde, butyr-aldehyde, pentanal, hexanal, heptanal, octanal or nonanal, oxiranes such as, for example, oxirane, 2-methyloxirane, 2-ethyloxirane, 2-propyloxirane, 2-butyloxirane, 2-pentyloxirane, 2-hexyloxirane or 2-heptyloxirane.

Suitable silylating agents are the compounds of the formulae IIIm, preferably trialkylsilyl halides, where the alkyl groups are straight-chain or branched and have from 1 to 8 carbon atoms, in particular the compounds of the formulae IIIm1 to IIIm8.

Suitable trialkyl borates are usually compounds of the formula IIIn1 $B(OR^3)_2(OR^4)$, preferably $B(OR^3)_3$, where $R^3$ is methyl, ethyl, propyl, butyl or isopropyl, in particular methyl or isopropyl.

A further advantage of the process according to the invention is that it can be safely interrupted at any time and resumed later since at any point in time in the reaction there are only minimal amounts of the reactive intermediate arylmetal compound.

In a preferred embodiment of the process according to the invention, the deprotonation of a halo- or trifluoromethoxy aromatic is achieved by firstly adding to the solution of the aromatic from 1 to 100 mol %, preferably from 1 to 50 mol %, in particular from 5 to 20 mol %, of an amine which can be converted into a metal amide by deprotonation, and introducing this mixture into the continuous-flow reactor in a defined mass or volume stream. The base used is preferably a solution of an alkyllithium compound, which is preferably introduced into the continuous-flow reactor in a mass or volume stream which contains a molar ratio of the base to the aromatic of from 1:1 to 1:2, preferably from 1:1 to 1:1.2. In the process, an intermediate formed from the added amine is the corresponding lithium amide, which deprotonates the halo- or trimethoxyaromatic and is then converted into the amide again by further alkyllithium. After a reaction zone which is sufficient for the complete lithiation of the aromatic, a solution of the electrophilic reagent is introduced into the continuous-flow reactor in a mass or volume stream which contains a molar ratio of the electrophilic reagent to the metalated aromatic of from 1:1 to 1:0.5, preferably from 1:1 to 1:0.8. After passing through a further reaction zone in which the electrophilic reagent is reacted with the arylmetal compound, the product stream leaves the continuous-flow reactor.

In a further preferred embodiment of the process according to the invention, the halogen-metal exchange is achieved by introducing the haloaromatic into the continuous-flow reactor preferably in the form of a solution in a defined mass or volume stream.

The metalating reagent used is preferably a solution of an alkyllithium compound, which is preferably introduced into the continuous-flow reactor in a mass or volume stream which contains a molar ratio of the metalating reagent to the aromatic of from 1:1 to 1:2, preferably from 1:1 to 1:1.2.

After passing through a reaction zone which suffices for the complete lithiation of the aromatic, a solution of the electrophilic reagent is introduced into the continuous-flow reactor in a mass or volume stream which contains a molar ratio of the electrophilic reagent to the metalated aromatic of from 1:1 to 1:0.5, preferably from 1:1 to 1:0.8. After passing through a further reaction zone in which the electrophilic reagent is reacted with the arylmetal compound, the product stream leaves the continuous-flow reactor.

Work-up of the reaction mixture and isolation of the products is carried out in the customary manner, e.g. by pouring the reaction mixture, which, if ketones, aldehydes or epoxides are used as electrophilic reagent, comprises the corresponding lithium alkoxides as product, onto water and/or ice or dilute acid and, following removal of the aqueous phase, isolating the products in the form of the respective alcohols by distillation or crystallization.

If amides are used as electrophilic reagents, the corresponding metalated hemiaminals initially form which, after protonation, fragment into the respective aldehydes.

According to the process of the invention, it is surprisingly possible to prepare substituted aromatics which are useful intermediates, for example, for liquid crystals, auxiliaries, crop protection compositions and pharmaceuticals, in a manner which is more simple than the prior art and in a manner which is safe on a relatively large scale and in relatively high yields.

The entire disclosure of all applications, patents and publications, cited above and below, and of corresponding German application No. 198 58 856.9, filed Dec. 19, 1998 is hereby incorporated by reference.

EXAMPLES

The examples below serve to illustrate the invention without limiting it. Above and below, percentages are percentages by weight. All temperatures are given in degrees Celsius. M.p.=melting point.

"Customary work-up" means that water is added if necessary, the mixture is extracted with methylene chloride, diethyl ether or toluene, the organic phase is separated off, dried and evaporated, and the product is purified by distillation under reduced pressure or crystallization and/or chromatography.

The following abbreviations are used:

| | |
|---|---|
| THF | tetrahydrofuran |
| KOtBu | potassium tert-butoxide |
| RT | room temperature |
| MTBE | methyl tert-butyl ether |

Example 1

1.1 kg/h of a 1 M solution of 2,3-difluorophenetole containing 10 mol % of 2,2,6,6-tetramethylpiperidine were introduced into a continuous-flow reactor and mixed with 0.4 kg/h of a 2.5 M solution of hexyllithium in hexane at −35° C. After the mixture had passed through the reaction zone, 0.28 kg/h of a 4.7 M solution of benzaldehyde in THF was mixed in. After the reaction had finished, the product was collected and worked up in the customary manner, giving 2,3-difluoro-4-ethoxy-α-phenylbenzyl alcohol. The conversion based on the starting compound was 97%.

The compounds below are obtained in an analogous manner by the process according to the invention using the corresponding precursors.

Examples 2–21

$R^0$—(A–Z)$_n$—[cyclohexyl(OH)]—[phenyl(F)(L)]—$R^2$

| | R⁰ | (A–Z)ₙ | R² | L |
|---|---|---|---|---|
| (2) | n-propyl | — | n-propyl | F |
| (3) | n-pentyl | — | n-propyl | F |
| (4) | n-pentyloxy | — | n-pentyloxy | F |
| (5) | CH=CH₂ | — | CH=CH₂ | H |
| (6) | OCH₂CH=CH₂ | — | CH₂CH=CH₂ | H |
| (7) | Methyl | — | OCH₂CH=CH₂ | F |
| (8) | n-Pentyloxy | cyclohexyl | n-propoxy | H |
| (9) | CH=CH₂ | cyclohexyl | O-n-butyl | H |
| (10) | n-butyl | 1,3-dioxane | CH=CH₂ | H |
| (11) | n-hexyl | 1,3-dioxane | CH₂CH=CH₂ | H |
| (12) | n-propoxy | phenylene | methyl | F |
| (13) | F | phenylene | E-CH₂CH=CHCH₃ | F |
| (14) | n-propyl | bicyclohexyl | n-propyl | H |

-continued

| | R⁰ | (A–Z)ₙ | R² | L |
|---|---|---|---|---|
| (15) | n-propoxy |  | n-pentyloxy | F |
| (16) | CH₂CH=CH₂ |  | n-propyl | F |
| (17) | n-propoxy |  | methyl | F |
| (18) | CH₂CH=CH₂ | | CH₂CH=CH₂ | F |

Examples 19–31

| | R⁰ | (A–Z)ₙ | R² | L |
|---|---|---|---|---|
| (19) | n-pentyloxy | — | n-propyl | F |
| (20) | n-pentyl | — | n-propyl | F |
| (21) | n-propyl | — | n-pentyloxy | F |
| (22) | methyl | — | CH=CH₂ | H |
| (23) | OCH₂CH=CH₂ | — | CH₂CH=CH₂ | H |
| (24) | CH=CH₂ | — | OCH₂CH=CH₂ | F |
| (25) | n-propyl | — | n-propyl | H |
| (26) | CH₂CH=CH₂ | — | n-pentyl | F |
| (27) | n-pentyloxy | — | n-propyl | F |
| (28) | n-propyl | — | methyl | F |
| (29) | n-hexyl | — | CH₂CH=CH₂ | F |
| (30) | CH=CH₂ | | n-propoxy | H |

Examples 31–42

| | R⁰ | (A–Z)$_n$ | R² | L |
|---|---|---|---|---|
| (31) | n-propyl | — | n-propyl | F |
| (32) | n-pentyl | — | n-propyl | F |
| (33) | n-pentyloxy | — | n-propoxy | F |
| (34) | CH=CH$_2$ | — | CH=CH$_2$ | H |
| (35) | OCH$_2$CH=CH$_2$ | — | CH$_2$CH=CH$_2$ | H |
| (36) | n-propyl | — | n-propyl | H |
| (37) | n-propoxy | — | n-pentyloxy | F |
| (38) | CH$_2$CH=CH$_2$ | — | n-propyl | F |
| (39) | n-propyl | — | methyl | F |
| (40) | CH$_2$CH=CH$_2$ | — | CH$_2$CH=CH$_2$ | F |
| (41) | methyl | — | OCH$_2$CH=CH$_2$ | F |
| (42) | n-pentyloxy | (cyclohexyl) | n-propyl | H |

Examples 43–55

| | R⁰ | L¹ | L² | L³ | R² |
|---|---|---|---|---|---|
| (43) | methyl | H | F | H | CH=CH$_2$ |
| (44) | OCH$_2$CH=CH$_2$ | F | H | H | CH$_2$CH=CH$_2$ |
| (45) | CH=CH$_2$ | F | H | H | OCH$_2$CH=CH$_2$ |
| (46) | n-propyl | H | F | F | CF$_3$ |
| (47) | CH$_2$CH=CH$_2$ | F | H | H | n-pentyloxy |
| (48) | n-propyl | H | H | H | n-propyl |
| (49) | n-propyl | H | H | H | methyl |
| (50) | n-hexyl | H | F | F | CH$_2$CH=CH$_2$ |
| (51) | CH=CH$_2$ | H | H | H | O-n-propyl |
| (52) | n-propoxy | F | H | H | O-n-butyl |
| (53) | n-propyl | H | F | F | CH=CH$_2$ |
| (54) | n-hexyl | H | H | H | CH$_2$CH=CH$_2$ |
| (55) | n-butyl | H | H | H | methyl |

Examples 56–72

| | R⁰ | (A–Z)$_n$ | L¹ | L² |
|---|---|---|---|---|
| (56) | n-propyl | — | F | H |
| (57) | n-pentyl | — | F | H |
| (58) | n-pentyloxy | — | F | H |
| (59) | CH=CH$_2$ | — | H | F |
| (60) | OCH$_2$CH=CH$_2$ | — | H | F |
| (61) | n-propyl | — | F | H |
| (62) | n-propoxy | — | F | H |
| (63) | CH$_2$CH=CH$_2$ | — | F | H |
| (64) | n-butyl | — | F | H |
| (65) | n-butyloxy | — | F | H |
| (66) | n-pentyl | — | H | F |
| (67) | ethyl | — | F | H |
| (68) | CH=CH$_2$ | — | H | F |
| (69) | methyl | — | H | H |
| (70) | OCH$_2$CH=CH$_2$ | — | F | H |
| (71) | n-butyl | (phenyl) | H | F |
| (72) | methoxy | (phenyl) | H | F |

Examples 73–78

(73) 4-n-Propyl-2,6-difluorobenzeneboronic anhydride
(74) 4-(4-Propylcyclohexyl)-2,3-difluorobenzeneboronic anhydride
(75) 4-Propyl-2,3-difluorobenzeneboronic anhydride
(76) 4-(4-Ethylphenyl)-2,3-difluorobenzeneboronic anhydride
(77) 4-(2-(4-(4-Propylcyclohexyl)cyclohexyl)ethyl)-2,3-difluorobenzeneboronic anhydride
(78) 4-Ethoxy-2,3-difluorophenylboronic anhydride

Example 79

3,5-Difluoro(4-propylcyclohexyl)benzene and 2 mol % of 2,2,6,6-tetramethylpiperidine were mixed with n-hexyllithium in a tubular reactor at −50° C. and, after a residence time of about 10 min, reacted with N-formylpiperidine. The conversion was >98%.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A process for the preparation of an arylmetal compound comprising:
    deprotonating an aromatic compound having a hydrogen atom in the ortho position relative to a halogen atom or a trifluoromethoxy group, using a base or by halogen-metal exchange of a haloaromatic using a metalating reagent,
    wherein said arylmetal compound is prepared in a continuous-flow reactor.

2. A process comprising reacting an arylmetal compound obtained by the process of claim 1 with an electrophilic reagent.

3. A process according to claim 1, wherein said arylmetal compound is an ortho-haloarylmetal compound.

4. A process according to claim 2, wherein said arylmetal compound is an ortho-haloarylmetal compound.

5. A process according to claim 2, wherein said electrophilic reagent is a ketone, a carboxamide or an aldehyde.

6. A process according to claim 2, wherein the compound obtained by reaction with the electrophilic reagent is a compound of formula I, where
    Q is F, Cl or Br,
    R$^1$ is H, F, Cl, Br, CN, alkyl, alkenyl, alkoxy, alkenyloxy having in each case up to 18 carbon atoms or a mesogenic group,
    W, X and Y in each case independently of one another are N, CH, CCN or CF, and in which
R$^2$ is alkyl, alkoxy, alkenyl, alkenyloxy having from 1 to 15 carbon atoms or a mesogenic radical,
M is Li, K, MgBr, MgCl or MgI,
s is 0 or 1,
BX$_2^2$ is a group of the formula —B(OR$^3$)(OR$^4$), or is a trioxatriborinone radical of the formula in which Z is R$^3$ and R$^4$ are each independently H, alkyl, alkenyl or cycloalkyl having in each case up to 10 carbon atoms or, taken together, are an alkylenediyl group of the formula —(CH$_2$)$_n$— or —CH$_2$CHR$^5$—CH$_2$—, in which n is 2, 3 or 4 and R$^5$ is alkyl, alkoxy or alkenyl having up to 18 carbon atoms or a mesogenic radical,
S' is a trihydrocarbylsilyl group of the formula —Si(R$^6$)$_3$ in which R$^6$ in each case independently of one another is an aliphatic, cycloaliphatic, araliphatic or aromatic radical,
TiX$_3^3$ is a radical of the formula TiBr$_3$, TiCl$_3$ or Ti(OR$_3$)$_3$, and
ZnX$^4$ is a radical of the formula ZnBr, ZnCl, ZnR$^3$ or ZnOR$^3$.

7. A process according to claim 6, wherein said compound of formula I is prepared in a continuous-flow reactor.

8. A process according to claim 6, wherein R$^1$, R$^2$ and/or R$^5$ is in each case independently, a mesogenic group of the formula II, where

R⁰—A¹—Z¹—(A²—Z²)ₘ—    II

R⁰ is F, CN, an alkyl or alkenyl radical having up to 15 carbon atoms which is unsubstituted or monosubstituted by CN, halogen or CF₃, where in these radicals, in addition, one or more —CH₂— groups in each case independently of one another can be replaced by —S—, —O—, —CO—, —CO—O—, —O—CO— or —O—CO—O— such that S and/or O atoms are not linked directly to one another, Z¹ and Z² in each case independently of one another are —CH₂CH₂—, —C≡C—, —CH₂O—, —OCH₂—, —CO—O—, —O—CO—, —CH=N—, —N=CH—, —CH₂S—, —SCH₂—, a single bond or an alkylene group having from 3 to 6 carbon atoms, in which, in addition, a —CH₂— group can be replaced by —O—, —CO—CO—, —O—CO—, —CHhalogen— or —CHCN—, A¹ and A² in each case independently of one another are
  a) a trans-1,4-cyclohexylene radical, in which, in addition, one or more non-adjacent —CH₂— groups can be replaced by —O— and/or —S—,
  b) a 1,4-phenylene radical, in which, in addition, one or two —CH= groups can be replaced by N,
  c) a radical from the group consisting of 1,3-cyclobutylene, 1,3-bicyclo(1,1,1)pentylene, 1,4-cyclohexenylene, 1,4-bicyclo(2,2,2)octylene, piperidine-1,4-diyl, naphthalene-2,6-diyl, decahydronaphthalene-2,6-diyl and 1,2,3,4-tetrahydronaphthalene-2,6-diyl where the radicals (a) and (b) can be substituted by CN or F, and m is 0, 1 or 2.

9. A process according to claim 7, wherein R¹, R² and/or R⁵ is in each case independently, a mesogenic group of the formula II, where

R⁰—A¹—Z¹—(A²—Z²)ₘ—    II

R⁰ is F, CN, an alkyl or alkenyl radical having up to 15 carbon atoms which is unsubstituted or monosubstituted by CN, halogen or CF₃, where in these radicals, in addition, one or more —CH₂— groups in each case independently of one another can be replaced by —S—, —O—, —CO—, —CO—O—, —O—CO— or —O—CO—O—such that S and/or O atoms are not linked directly to one another, Z¹ and Z² in each case independently of one another are —CH₂CH₂—, —C≡C—, —CH₂O—, —OCH₂—, —CO—O—, —O—CO—, —CH=N—, —N=CH—, —CH₂S—, —SCH₂—, a single bond or an alkylene group having from 3 to 6 carbon atoms, in which, in addition, a —CH₂— group can be replaced by —O—, —CO—O—, —O—CO—, —CHhalogen— or —CHCN—, A¹ and A² in each case independently of one another are
  a) a trans-1,4-cyclohexylene radical, in which, in addition, one or more non-adjacent —CH₂— groups can be replaced by —O— and/or —S—,
  b) a 1,4-phenylene radical, in which, in addition, one or two —CH= groups can be replaced by N,
  c) a radical from the group consisting of 1,3-cyclobutylene, 1,3-bicyclo(1,1,1)pentylene, 1,4-cyclohexenylene, 1,4-bicyclo(2,2,2)octylene, piperidine-1,4-diyl, naphthalene-2,6-diyl, decahydronaphthalene-2,6-diyl and 1,2,3,4-tetrahydronaphthalene-2,6-diyl where the radicals (a) and (b) can be substituted by CN or F, and m is 0, 1 or 2.

10. A process according to claim 1, wherein a metal amide, an alkylmetal compound or an arylmetal compound is used for the deprotonation of the halo- or trifluoromethoxyaromatic.

11. A process according to claim 10, wherein said metal amide is prepared in the presence of the aromatic to be metalated by reaction of a corresponding amine with an alkylmetal compound.

12. A process according to claim 11, wherein a catalytic amount of the amine is used.

13. A process according claim 1, wherein an alkylmetal compound is used for the halogen-metal exchange.

14. A process according to claim 1, wherein the starting materials are reacted at temperatures of −40° C. to +40° C. in said continuous-flow reactor.

15. A process according to claim 1, wherein the starting materials are introduced into the continuous-flow reactor as a solution in an inert solvent.

16. A process according to claim 1, wherein said arylmetal compound is an aryllithium compound.

* * * * *